United States Patent
Eidenschink (10) Patent No.: US 9,662,205 B2
(45) Date of Patent: May 30, 2017

(54) APPARATUS AND METHOD FOR HEART VALVE REPAIR

(71) Applicant: St. Jude Medical, Cardiology Division, Inc., St. Paul, MN (US)

(72) Inventor: Tracee Eidenschink, Wayzata, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 176 days.

(21) Appl. No.: 13/782,144

(22) Filed: Mar. 1, 2013

(65) Prior Publication Data

US 2014/0039608 A1  Feb. 6, 2014

Related U.S. Application Data

(60) Provisional application No. 61/678,842, filed on Aug. 2, 2012.

(51) Int. Cl.
*A61B 17/08* (2006.01)
*A61F 2/24* (2006.01)
(Continued)

(52) U.S. Cl.
CPC ...... *A61F 2/2427* (2013.01); *A61B 17/00234* (2013.01); *A61B 17/0643* (2013.01);
(Continued)

(58) Field of Classification Search
CPC ..... A61B 17/0401; A61B 17/08; A61B 17/10; A61B 17/12; A61B 17/12009;
(Continued)

(56) References Cited

U.S. PATENT DOCUMENTS

| 5,156,608 A | 10/1992 | Troidl et al. |
| 5,499,991 A | 3/1996 | Garman et al. |

(Continued)

FOREIGN PATENT DOCUMENTS

| AU | 2002300522 B2 | 1/2007 |
| WO | 9620749 A1 | 7/1996 |

(Continued)

OTHER PUBLICATIONS

International Search Report for Application No. PCT/US2012/023437 dated Apr. 24, 2012.

(Continued)

*Primary Examiner* — Melanie Tyson
(74) *Attorney, Agent, or Firm* — Lerner, David, Littenberg, Krumholz & Mentlik, LLP (57) ABSTRACT

A device for gathering tissue of a heart valve leaflet may include an outer tube extending in an elongated direction, a capture tool moveable in the outer tube between a contained position and a use position, and a tissue securing component disposed at a distal end of the outer tube and adapted to be applied to tissue captured by the capture tool and to hold the captured tissue in a gathered configuration. The capture tool may include two grasping members that are moveable relative to one another in the elongated direction. Each grasping member may have a proximal portion and a plurality of fingers or barbs. The grasping members may be operable to capture tissue of the heart valve leaflet therebetween and to draw the captured tissue into the outer tube in the gathered configuration.

6 Claims, 4 Drawing Sheets

(51) Int. Cl.
*A61B 17/00* (2006.01)
*A61B 17/064* (2006.01)
*A61B 17/12* (2006.01)
*A61B 17/068* (2006.01)
*A61B 17/29* (2006.01)

(52) U.S. Cl.
CPC ...... *A61B 17/12013* (2013.01); *A61B 17/068* (2013.01); *A61B 2017/00243* (2013.01); *A61B 2017/00349* (2013.01); *A61B 2017/00783* (2013.01); *A61B 2017/0645* (2013.01); *A61B 2017/12018* (2013.01); *A61B 2017/2924* (2013.01); *A61B 2017/2926* (2013.01); *A61F 2/2454* (2013.01)

(58) Field of Classification Search
CPC ........ A61B 17/12013; A61B 17/12018; A61B 17/128; A61B 17/1285; A61B 2017/00623; A61B 2017/00349; A61F 2/2427
USPC ....... 606/142, 143, 144, 145, 148, 156, 157, 606/158, 139–141, 228; 600/337
See application file for complete search history.

(56) References Cited

U.S. PATENT DOCUMENTS

| | | | |
|---|---|---|---|
| 5,601,573 A | 2/1997 | Fogelberg et al. | |
| 5,741,278 A | 4/1998 | Stevens | |
| 5,749,879 A | 5/1998 | Middleman et al. | |
| 5,921,993 A | 7/1999 | Yoon | |
| 6,258,105 B1 | 7/2001 | Hart et al. | |
| 6,440,152 B1* | 8/2002 | Gainor et al. | 606/213 |
| 6,569,182 B1 | 5/2003 | Balceta et al. | |
| 6,626,930 B1 | 9/2003 | Allen et al. | |
| 6,752,813 B2 | 6/2004 | Goldfarb et al. | |
| 6,945,978 B1 | 9/2005 | Hyde | |
| 7,011,669 B2 | 3/2006 | Kimblad | |
| 7,464,712 B2 | 12/2008 | Oz et al. | |
| 7,569,062 B1 | 8/2009 | Kuehn et al. | |
| 7,758,595 B2* | 7/2010 | Allen et al. | 606/139 |
| 8,777,966 B2 | 7/2014 | Dale et al. | |
| 8,951,285 B2 | 2/2015 | Sugimoto et al. | |
| 2001/0016750 A1 | 8/2001 | Malecki et al. | |
| 2002/0010388 A1 | 1/2002 | Taylor et al. | |
| 2002/0013571 A1 | 1/2002 | Goldfarb et al. | |
| 2002/0035390 A1 | 3/2002 | Schaldach et al. | |
| 2002/0049457 A1 | 4/2002 | Kaplan et al. | |
| 2002/0107531 A1 | 8/2002 | Schreck et al. | |
| 2002/0183768 A1 | 12/2002 | Deem et al. | |
| 2003/0093071 A1 | 5/2003 | Hauck et al. | |
| 2003/0120264 A1 | 6/2003 | Lattouf | |
| 2004/0030335 A1 | 2/2004 | Zenati et al. | |
| 2004/0039442 A1 | 2/2004 | St. Goar et al. | |
| 2004/0087985 A1* | 5/2004 | Loshakove | A61B 17/0057 606/153 |
| 2004/0176784 A1 | 9/2004 | Okada | |
| 2004/0181238 A1 | 9/2004 | Zarbatany et al. | |
| 2004/0193185 A1 | 9/2004 | McBrayer | |
| 2005/0004583 A1 | 1/2005 | Oz et al. | |
| 2005/0090837 A1 | 4/2005 | Sixto et al. | |
| 2005/0096671 A1 | 5/2005 | Wellman et al. | |
| 2005/0107871 A1 | 5/2005 | Realyvasquez et al. | |
| 2005/0125011 A1 | 6/2005 | Spence et al. | |
| 2005/0143763 A1 | 6/2005 | Ortiz et al. | |
| 2005/0149072 A1 | 7/2005 | DeVries et al. | |
| 2005/0177176 A1 | 8/2005 | Gerbi et al. | |
| 2005/0251161 A1 | 11/2005 | Saadat et al. | |
| 2006/0009800 A1* | 1/2006 | Christianson | A61B 17/0057 606/213 |
| 2006/0089671 A1* | 4/2006 | Goldfarb | A61B 17/122 606/215 |
| 2006/0122633 A1 | 6/2006 | To et al. | |
| 2006/0173422 A1 | 8/2006 | Reydel et al. | |
| 2006/0173473 A1 | 8/2006 | Bob | |
| 2007/0049952 A1 | 3/2007 | Weiss | |
| 2007/0093857 A1* | 4/2007 | Rogers | A61B 17/0644 606/142 |
| 2007/0102474 A1 | 5/2007 | Shelton et al. | |
| 2007/0102475 A1 | 5/2007 | Ortiz et al. | |
| 2007/0142846 A1 | 6/2007 | Catanese et al. | |
| 2007/0162056 A1 | 7/2007 | Gerbi et al. | |
| 2007/0197858 A1* | 8/2007 | Goldfarb et al. | 600/37 |
| 2007/0198032 A1 | 8/2007 | Ortiz | |
| 2007/0225734 A1 | 9/2007 | Bell et al. | |
| 2008/0125796 A1 | 5/2008 | Graham | |
| 2008/0234705 A1 | 9/2008 | Cropper et al. | |
| 2008/0255427 A1* | 10/2008 | Satake | A61B 17/08 600/204 |
| 2008/0294175 A1 | 11/2008 | Bardsley et al. | |
| 2008/0300624 A1 | 12/2008 | Schwemberger et al. | |
| 2008/0319455 A1* | 12/2008 | Harris | A61B 17/0684 606/139 |
| 2009/0062852 A1 | 3/2009 | Marino | |
| 2009/0118744 A1 | 5/2009 | Wells et al. | |
| 2009/0125038 A1 | 5/2009 | Ewers et al. | |
| 2009/0149870 A1 | 6/2009 | Jugenheimer et al. | |
| 2011/0054521 A1 | 3/2011 | Ventura et al. | |
| 2011/0077668 A1* | 3/2011 | Gordon | A61B 17/0057 606/142 |
| 2011/0087242 A1 | 4/2011 | Pribanic et al. | |
| 2011/0114700 A1 | 5/2011 | Baxter, III et al. | |
| 2011/0230897 A1 | 9/2011 | Palermo et al. | |
| 2011/0313432 A1 | 12/2011 | Miles et al. | |
| 2012/0109159 A1 | 5/2012 | Jordan et al. | |
| 2012/0226291 A1 | 9/2012 | Malizia et al. | |
| 2013/0046332 A1 | 2/2013 | Jones et al. | |
| 2014/0039607 A1 | 2/2014 | Kovach | |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 0200121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report and Written Opinion for Application No. PCT/US2013/065360 dated Apr. 23, 2014.
International Search Report and Written Opinion for Application No. PCT/US2013/052843 dated Oct. 11, 2013.
International Search Report and Written Opinion for Application No. PCT/US2013/052838 dated Oct. 11, 2013.
International Search Report and Written Opinion for Application No. PCT/US2013/052822 dated Jan. 21, 2014.
International Preliminary Report on Patentability for Application No. PCT/US2012/023437 dated Aug. 6, 2013.
International Search Report for Application No. PCT/US2013/023077 dated May 14, 2013.
International Search Report and Written Opinion for Application No. PCT/US2013/023082 dated Oct. 1, 2013.
International Search Report and Written Opinion for Application No. PCT/US2013/024304 dated Jul. 5, 2013.
International Search Report for Application No. PCT/US2013/052832 dated Jan. 15, 2014.

(56) References Cited

OTHER PUBLICATIONS

Merriam-Webster definition of "fabric" as accessed on Dec. 17, 2014; http://www.merriam-webster.com/dictionary/fabric.

* cited by examiner

APPARATUS AND METHOD FOR HEART VALVE REPAIR

CROSS-REFERENCE TO RELATED APPLICATION

The present application claims the benefit of the filing date of U.S. Provisional Patent Application No. 61/678,842, filed Aug. 2, 2012, the disclosure of which is hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be broken. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to flow back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

Methods and devices for gathering of heart valve leaflet tissue are disclosed. A device for gathering tissue of a heart valve leaflet may include an outer tube extending in an elongated direction and a capture tool moveable in the outer tube between a contained position and a use position. The capture tool may include two grasping members that are moveable relative to one another in the elongated direction. The device may also include a tissue securing component disposed at a distal end of the outer tube and adapted to be applied to tissue captured by the capture tool and to hold the captured tissue in a gathered configuration.

In one embodiment, each grasping member may have a proximal portion and a plurality of fingers. Some fingers may extend from the proximal portion in a different plane than other fingers. The grasping members may be operable to capture tissue of the heart valve leaflet therebetween and to draw the captured tissue into the outer tube in the gathered configuration.

The capture tool may also include two actuation rods slidably coupled to one another by a coupling member. Each actuation rod may extend within the outer tube in the elongated direction. Each grasping member may be attached at the proximal portion thereof to a respective one of the actuation rods. Each grasping member may be moveable between a retracted position in which the grasping member lies within the outer tube, and a deployed position in which the grasping member lies outside of the outer tube. The fingers of each grasping member may extend at an obtuse angle relative to the proximal portion in the retracted position. The fingers of each grasping member may extend at substantially a right angle relative to the proximal portion in the deployed position. One or more of the fingers of at least one of the grasping members may have a surface that is knurled or roughened.

In a particular embodiment, the tissue securing component may be a releasable clip. The clip may be biased from a partially open condition to a clamping condition. The clip may be configured to be held in the partially open condition around an outer surface of the outer tube until the clip is released.

Another device for gathering tissue of a heart valve leaflet may include an outer tube extending in an elongated direction and a capture tool moveable in the outer tube between a contained position and a use position. The capture tool may include two grasping members that are moveable relative to one another in the elongated direction. The device may also include a tissue securing component disposed at a distal end of the outer tube and adapted to be applied to the grasping members to hold the captured tissue in a gathered configuration.

In one embodiment, each grasping member may have a barb at each of two opposing ends thereof. The grasping members may be operable to capture tissue of the heart valve leaflet therebetween and to draw the captured tissue into the outer tube in the gathered configuration. Each grasping member may be moveable between a retracted position in which the grasping member lies within the outer tube, and a deployed position in which the grasping member lies outside of the outer tube. Each grasping member may have a V-shape in the retracted position and may extend substantially in a linear direction in the deployed position.

The device may also include two actuation rods. Each actuation rod may be longitudinally slidable within the outer tube and may be adapted to be removably coupled to a respective one of the grasping members. A distal end of each actuation rod may be threaded and may be adapted to engage with a tapped recess of the respective one of the grasping members. The tissue securing component may be a locking ring that is configured to slide over at least one of the grasping members to lock the grasping members into the V-shape and to retain the captured tissue in the gathered configuration.

Yet another device for gathering tissue of a heart valve leaflet may include an outer tube extending in an elongated direction and a capture tool including two grasping members movable relative to one another in the elongated direction between a contained position proximally within the outer tube and a use position distally of the outer tube. The two grasping members when in the use position may be arranged spaced apart from one another, and may be operative to capture tissue of the heart valve leaflet therebetween and to draw the captured tissue into the outer tube when in the contained position.

The device may also include a tissue securing component disposed at a distal end of the outer tube and adapted to be applied to the captured tissue to hold the captured tissue in a gathered configuration. The device may also include two actuation rods respectively connected to the grasping members for moving the grasping members between the contained position and the use position.

A transcatheter method of gathering tissue of a heart valve leaflet may include inserting an elongated catheter assembly to a position adjacent the heart valve leaflet. The catheter assembly may include an outer tube extending in an elongated direction and a capture tool moveable in the outer tube between a contained position and a use position. The method may also include moving the capture tool from the contained position to the use position. The capture tool may include two grasping members that are moveable relative to one another in the elongated direction. Each grasping member may change orientation or shape when moved from the contained position to the use position.

The method may also include manipulating the catheter assembly so that tissue of the heart valve leaflet is captured by the capture tool, retracting the capture tool from the use position toward the contained position to draw the captured tissue into the outer tube in a gathered configuration, and applying a tissue securing component from the distal end of the outer tube to the captured tissue to hold the captured tissue substantially in the gathered configuration.

In one embodiment, each grasping member may have a proximal portion and a plurality of fingers. Some fingers may extend from the proximal portion in a different plane than other fingers. The step of moving the capture tool from the contained position to the use position may move the fingers of each grasping member from extending at an obtuse angle relative to the proximal portion to extending at substantially a right angle relative to the proximal portion.

The step of retracting the capture tool may include (i) partially retracting the capture tool such that the grasping members contact the outer tube and change orientation, and (ii) rotating the capture tool about a longitudinal axis of the outer tube such that the captured tissue is moved to a twisted configuration. The tissue securing component may be a releasable clip biased from a partially open condition to a clamping condition. The step of applying the tissue securing component to the captured tissue may include releasing the clip from the outer tube so that it becomes clamped onto the captured tissue.

In a particular embodiment, the step of moving the capture tool from the contained position to the use position may move each grasping member from a V-shape to a substantially linear shape. The step of retracting the capture tool may include moving the grasping members into contact with the outer tube so that the grasping members move from the substantially linear shape to the V-shape.

The tissue securing component may be a locking ring that is configured to slide over at least one of the grasping members. The step of applying the tissue securing component to the captured tissue may include sliding the locking ring over at least one of the grasping members such that the grasping members are retained in the V-shape the captured tissue is retained in the gathered configuration. Each grasping member may be removably coupled to an actuation rod extending proximally therefrom within the outer tube. The step of retracting the capture tool from the use position toward the contained position may include sliding the actuation rods in a proximal direction of the outer tube. The method may also include, after the step of applying the tissue securing component to the captured tissue, removing each actuation rod from a respective one of the grasping members.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
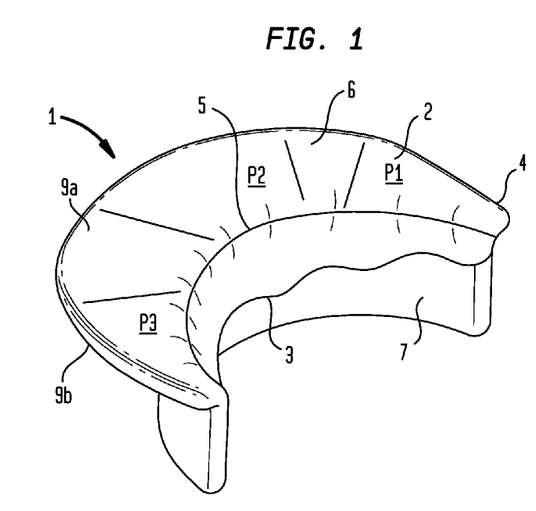
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 also has an upper surface 9a and an lower surface 9b. The posterior leaflet 2 has three scalloped portions P1, P2, and P3, any of which may include a portion that is billowed, loose, or floppy, and which therefore may be the cause of a prolapse condition of the valve. The inventive devices, systems, and methods described herein may be adapted to repair such a billowed, loose, or floppy portion of the posterior leaflet 2 or the anterior leaflet 3.

Referring to FIGS. 2A-2E, an exemplary device 10 for gathering of heart valve leaflet tissue includes an elongated catheter assembly 12 adapted to be inserted through the apex of a human heart so that a distal portion 14 of the catheter assembly may reach the patient's mitral valve 1 for repair thereof.

Figure 2A:
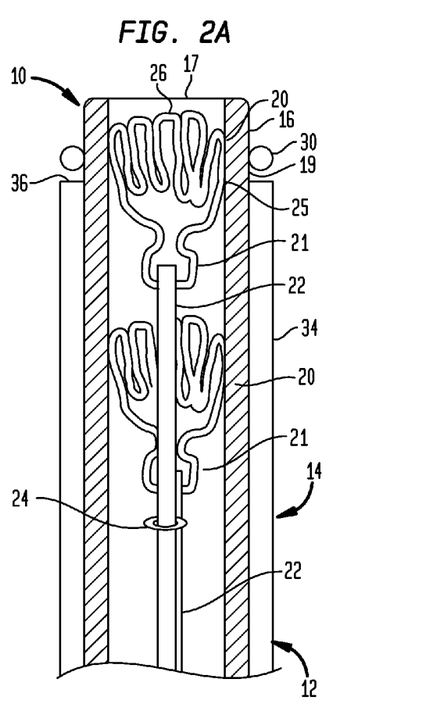
FIG. 2A is a longitudinal cross-sectional view of the distal portion of one embodiment of a device for transcatheter gathering of heart valve leaflet tissue.
Figure 2B:
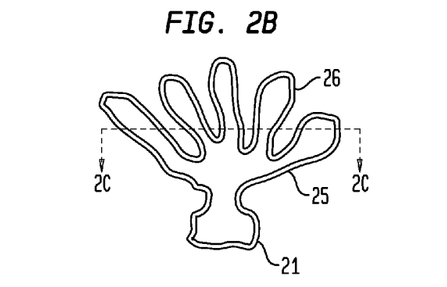
FIG. 2B is a side view of one of the grasping members of FIG. 2A.

The catheter assembly 12 includes a capture tool in the form of two grasping members 20 each disposed within an elongated outer tube 16. Each grasping member 20 may be independently longitudinally slidable within the outer tube 16 between a retracted position within the outer tube and a deployed position in which the grasping member protrudes distally beyond the open distal end 17 of the outer tube. The outer tube 16 may be made of one or more echogenic materials, so that the outer tube may be more easily visualized inside a patient using three-dimensional echocardiography.

Each grasping member 20 may be attached at its proximal end to a respective actuation rod 22 extending within the outer tube 16 from a proximal portion 21 of the grasping member to a proximal end of the device (not shown). The actuation rods 22 may be slidably coupled to one another by a coupling member in the form of a ring 24 that may encircle one actuation rod and may be attached to the other actuation rod at a side of the ring. The ring 24 may prevent the actuation rods 22 from separating from one another in a direction perpendicular to the longitudinal axis of the outer tube 16.

Figure 3A:
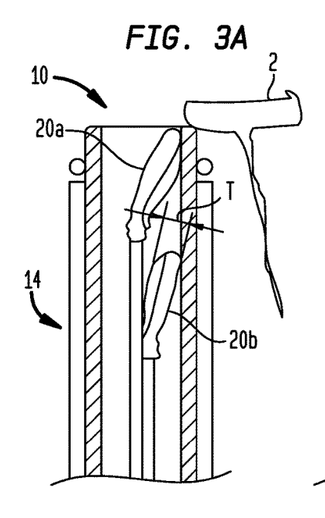
FIG. 3A is a longitudinal cross-sectional view of the device of FIG. 2A, shown adjacent the posterior leaflet of the mitral valve of FIG. 1.
Figure 3B:
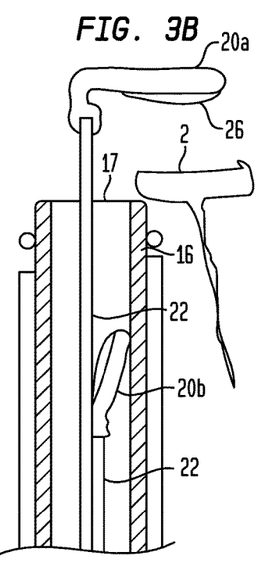
FIG. 3B is a longitudinal cross-sectional view of the device of FIG. 2A, shown with one of the grasping members deployed.
Figure 3C:
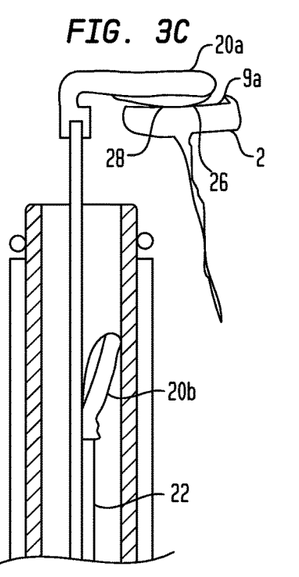
FIG. 3C is a longitudinal cross-sectional view of the device of FIG. 2A, shown with one of the grasping members engaged with leaflet tissue.
Figure 3D:
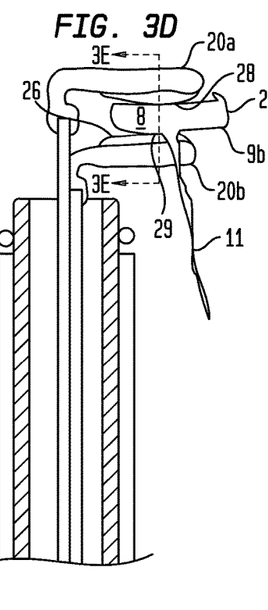
FIG. 3D is a longitudinal cross-sectional view of the device of FIG. 2A, shown with both grasping members engaged with leaflet tissue.

Each grasping member 20 may have an obtuse-angled orientation relative to the actuation rod 22 when in the retracted position within the outer tube 16, as shown in FIG. 3A, and each grasping member may assume a substantially right-angled orientation relative to the actuation rod when deployed from the outer tube, as shown in FIG. 3D. In that regard, each grasping member 20 may be formed from a memory metal or a strong, resilient metal or polymer that will cause the right-angled orientation to form automatically when deployed. The structure of each grasping member 20 may be formed in various ways, including for example, etching a sheet of metal (e.g., a nitinol sheet), cutting a sheet of metal with a laser, or forming a wire into the desired shape. If the grasping members 20 have a thickness T (FIG. 3A) that is relatively large compared to the diameter of the lumen of the outer tube 16, the grasping members may each have a substantially planar orientation when in the retracted position within the outer tube.

Figure 2C:
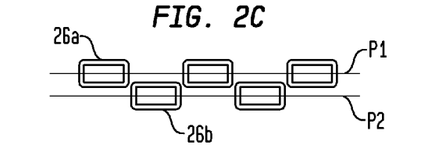
FIG. 2C is a cross-sectional view taken along line 2C-2C of FIG. 2B.
Figure 2D:
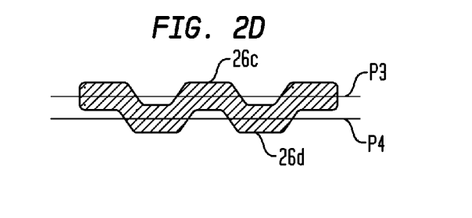
FIG. 2D is a cross-sectional view of a variation of one of the grasping members of FIG. 2A.
Figure 2E:
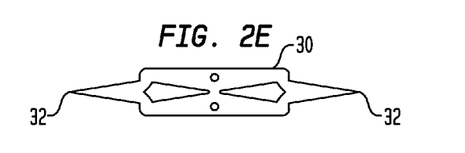
FIG. 2E is a plan view of the clip of FIG. 2A, shown in an open position.

The distal portion 25 of each grasping member 20 may be shaped into one or more fingers 26 that may extend from the proximal portion 21 of the grasping member in more than one plane. For example, as shown in FIG. 2C, some of the fingers 26a of each grasping member 20 may be disposed in a first plane P1, and others of the fingers 26b may be disposed in a second plane P2. The first plane P1 and the second plane P2 may or may not be parallel to one another.

The fingers 26 of each grasping member 20 may have a surface that is roughened or knurled to increase the friction with a captured leaflet portion. For example, as can be seen in FIG. 3D, a first grasping member 20a may have a roughened lower surface 28 facing a captured leaflet portion 8, and a second grasping member 20b may have a roughened upper surface 29 facing the captured leaflet portion. Each finger 26 may be solid, or it may include mesh portions having openings extending therethrough.

Although each grasping member 20 is shown in the figures as having five fingers 26, that need not be the case. Each grasping member 20 may have any number of fingers, including one, two, three, four, six, eight, ten, twelve, or fifteen, for example. Although the first grasping member 20a and the second grasping member 20b are shown in the figures as having an equal number of fingers 26, that need not be the case. The first grasping member 20a may have more or less fingers than the second grasping member 20b.

Although each grasping member 20 is shown in the figures as having a plurality of fingers 26 having respective distal tips 25a that are spaced apart from one another, that need not be the case. In one variant, one or both grasping members may have fingers that are joined to one another at the distal tips, or joined to one another along the entire length of the fingers. In another variant, shown in FIG. 2D, one or both grasping members may comprise a continuous sheet of material that is shaped such that some portions 26c of each grasping member may be disposed in a first plane P3, and others other portions 26d may be disposed in a second plane P4. The first plane P3 and the second plane P4 may or may not be parallel to one another. Such a continuous sheet of material may be solid, or it may include mesh portions having openings extending therethrough.

Figure 2F:
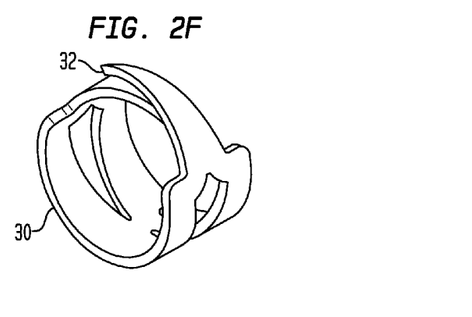
FIG. 2F is a perspective view of the clip of FIG. 2A, shown in a closed position.

A tissue securing component in the form of a clip 30 may be configured to be applied around a captured portion of the posterior leaflet 2. The clip 30 may be made of a memory metal and may be biased to curl into a substantially round configuration (FIG. 2F) from a completely open configuration (FIG. 2E) when deployed from the outer tube 16. A prong 32 at each end of the clip 30 may become embedded in the leaflet tissue when the clip is deployed. One or more clips 30 may be disposed in a partially open configuration (e.g., with the prongs 32 spaced apart from one another) around the outer surface 19 of the outer tube 16 adjacent the distal end 17 thereof. The outer tube 16 may be slidably disposed in a deployment tube 34 with a tight clearance, such that the clip 30 will interfere with the distal end 36 of the deployment tube as the deployment tube is moved toward the distal end 17 of the outer tube.

To use the device 10 to gather heart valve leaflet tissue, one or more clips 30 may be expanded into the partially open configuration and placed around the outer surface 19 of the outer tube 16 adjacent the distal end 17 thereof. For increased visibility of the components of the device 10, the ring 24 is not shown in FIGS. 3A-3K.

Next, the distal portion 14 of the catheter assembly 12 may be inserted into a patient, for example, through the apex of the heart into the left ventricle, so that the distal portion extends between the posterior leaflet 2 and the anterior leaflet 3 of the mitral valve 1. The distal end 17 of the outer tube 16 may be disposed near the coaption line 5 of the mitral valve 1, as shown in FIG. 3A, with the grasping members 20 biased to bend toward the posterior side of the aortic annulus 4. The distal end 17 of the outer tube 16 may be guided to a position near the coaption line 5 using three-dimensional echocardiography or another imaging technique to visualize the outer tube or other components of the catheter assembly 12.

Once the outer tube 16 has been properly positioned, the first grasping member 20a may be deployed by sliding the respective actuation rod 22 distally so that the grasping member slides beyond the distal end 17 of the outer tube 16. No longer being constrained by the outer tube 16, the first grasping member 20a may assume a substantially right-angled orientation, with the fingers 26 thereof extending above the target portion of the posterior leaflet 2 to be captured, as shown in FIG. 3B. For example, the target portion of the posterior leaflet 2 to be captured may be a loose edge of the leaflet below the coaption line 5. Next, the lower surface 28 of the fingers 26 of the first grasping member 20a may be placed adjacent the upper surface 9a of the target portion of the posterior leaflet 2, as can be seen in FIG. 3C, by moving the distal portion 14 of the catheter assembly 12 proximally relative to the posterior leaflet.

Then, as shown in FIG. 3D, the second grasping member 20b may be deployed by sliding the respective actuation rod 22 distally so that the grasping member slides beyond the distal end 17 of the outer tube 16. No longer being constrained by the outer tube 16, the second grasping member 20b may assume a substantially right-angled orientation, with the fingers 26 thereof extending below the target portion of the posterior leaflet 2 to be captured. The upper surface 29 of the fingers 26 of the second grasping member 20b may be placed adjacent the lower surface 9b of the target portion of the posterior leaflet 2 by sliding the respective actuation rod 22 distally relative to the posterior leaflet. If desired, the distal portion 25 of the second grasping member 20b can be guided to the lower surface 9b between adjacent chordae tendinae 11, so that the chordae tendinae are not damaged during application of the clip 30 as described below.

Figure 3E:
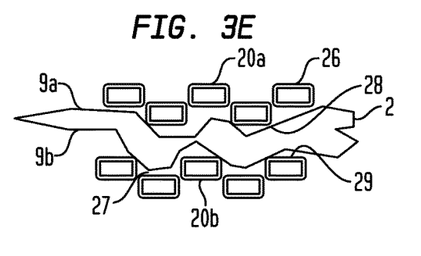
FIG. 3E is a cross-sectional view taken along line 3E-3E of FIG. 3D.

The user may capture the target portion of the posterior leaflet 2 by sliding the actuation rod 22 of the first grasping member 20a proximally and sliding the actuation rod of the second grasping member 20b distally until the target leaflet portion is sandwiched between the lower surface of the fingers 26 of the first grasping member and the upper surface 29 of the fingers of the second grasping member. As shown in FIG. 3E, some of the fingers 26 of the first grasping member 20a may be disposed opposite gaps 27 between some of the fingers of the second grasping member 20b, so that when the grasping members are sandwiched together, some of the target leaflet portion is forced into such gaps, thereby increasing the friction with the captured leaflet portion 8. Also, some of the fingers 26 of the second grasping member 20b may be disposed opposite gaps 27 between some of the fingers of the first grasping member 20a, so that when the grasping members are sandwiched together, some of the target leaflet portion is forced into such gaps, thereby increasing the friction with the captured leaflet portion 8.

Figure 3F:
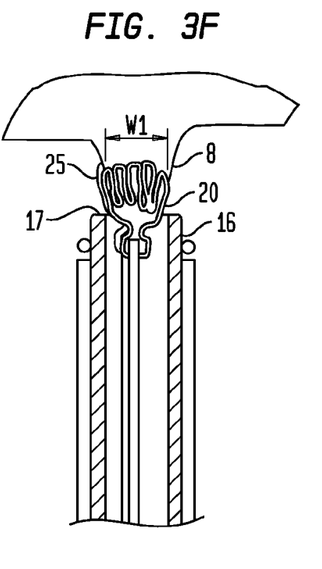
FIG. 3F is a longitudinal cross-sectional view of the device of FIG. 2A, shown with both grasping members partially retracted into the outer tube.

Subsequently, the grasping members 20 may be partially retracted into the outer tube 16, as shown in FIG. 3F, so that the distal portion 25 of each grasping member may contact the distal end 17 of the outer tube. As the grasping members 20 are retracted into the outer tube 16, contact with the outer tube 16 will cause the grasping members assume an obtuse-angled or substantially planar orientation.

Figure 3G:
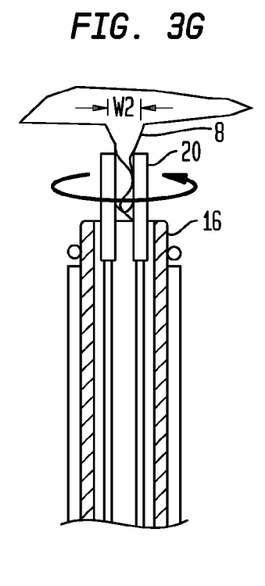
FIG. 3G is a longitudinal cross-sectional view of the device of FIG. 2A, shown with both grasping members in a step of twisting the captured leaflet tissue.

Then, as shown in FIG. 3G, the grasping members 20 may be rotated about the longitudinal axis of the outer tube 16, thereby causing the captured leaflet portion 8 to assume a twisted shape. Such a twisted captured leaflet portion 8 may have a width W2 in a plane normal to the longitudinal axis of the outer tube 16 that is smaller than its untwisted width W1 (FIG. 3F), which may make it easier for the clip 30 to fit around the captured leaflet portion, as will be described below.

Figure 3H:
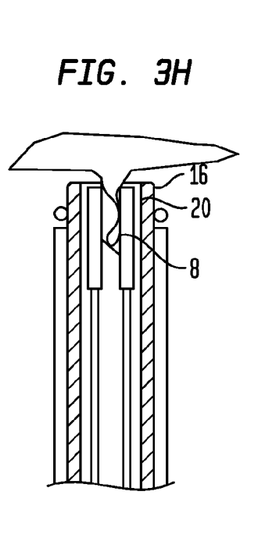
FIG. 3H is a longitudinal cross-sectional view of the device of FIG. 2A, shown with both grasping members and the captured leaflet tissue retracted into the outer tube.

Next, the grasping members 20 may be further retracted into the outer tube 16, as shown in FIG. 3H, such that most or all of the grasping members and a substantial amount of the captured portion 8 of the posterior leaflet 2 are pulled into the lumen of the outer tube.

Figure 3I:
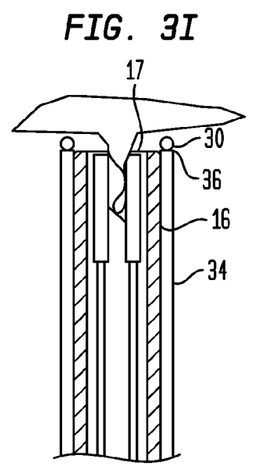
FIG. 3I is a longitudinal cross-sectional view of the device of FIG. 2A, shown with the clip deployed off of the distal end of the outer tube.

As shown in FIG. 3I, the user may secure the captured portion 8 of the posterior leaflet 2 by pushing the deployment tube 34 distally until the distal end 36 thereof contacts the clip 30 and pushes it in a distal direction off of the distal end 17 of the outer tube 16. As the clip 30 is released from the outer tube 16, it will collapse to a substantially round configuration according to its bias, and the two prongs 32 of the clip will become embedded in the captured tissue 8 of the posterior leaflet 2, thereby securing the tissue. If a plurality of clips 30 are disposed adjacent one another at the distal end 17 of the outer tube 16, additional clips can be deployed onto the posterior leaflet 2 by continuing to move the deployment tube 34 distally until each additional clip is pushed off of the outer tube as desired.

Figure 3J:
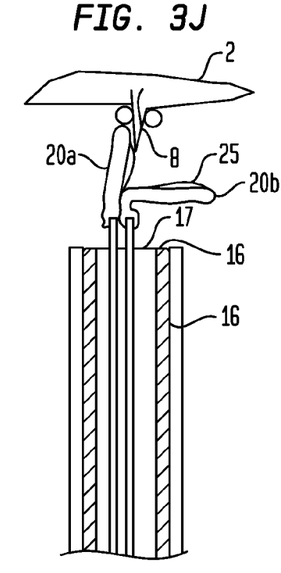
FIG. 3J is a longitudinal cross-sectional view of the device of FIG. 2A, shown with one of the grasping members disengaged from the secured tissue.

After one or more clips 30 have been adequately secured on the captured tissue 8 of the posterior leaflet 2, the device 10 may be withdrawn from the patient. As a first step, the second grasping member 20b may be disengaged from the posterior leaflet 2 by sliding the actuation rods 22 distally so that the grasping members 20a, 20b slide beyond the distal end 17 of the outer tube 16, as shown in FIG. 3J. No longer being constrained by the outer tube 16, the second grasping member 20b may assume a substantially right-angled orientation, with the distal portion 25 thereof bending away from the captured tissue 8 of the posterior leaflet 2.

Figure 3K:
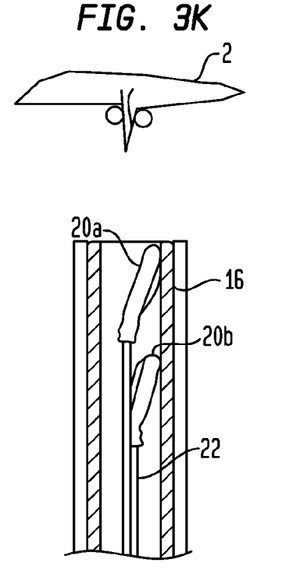
FIG. 3K is a longitudinal cross-sectional view of the device of FIG. 2A, shown with both grasping members disengaged from the secured tissue.

Next, the first grasping member 20a may be disengaged from the posterior leaflet 2 by sliding the actuation rods 22 proximally so that the grasping members are pulled into the lumen of the outer tube 16, as shown in FIG. 3K. The catheter assembly 12 may subsequently be withdrawn from the patient through the apex of the heart. The procedure described above may be repeated to apply one or more additional clips 30 onto a different portion of the same posterior leaflet 2.

Figures 4, 5A:
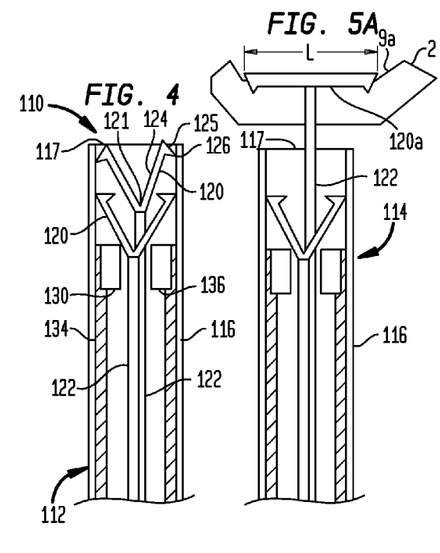
FIG. 4 is a longitudinal cross-sectional view of the distal portion of another embodiment of a device for transcatheter gathering of heart valve leaflet tissue.
FIG. 5A is a longitudinal cross-sectional view of the device of FIG. 4, shown with one of the grasping members engaged with leaflet tissue.

Another embodiment of a capture tool and tissue securing component is shown in FIG. 4. The catheter assembly 112 of the device 110 includes a capture tool in the form of two releasable grasping members 120 each disposed within an elongated outer tube 116. Each grasping member 120 may be independently longitudinally slidable within the outer tube 116 between a retracted position within the outer tube and a deployed position in which the grasping member protrudes distally beyond the open distal end 117 of the outer tube. The outer tube 116 may be the same as the outer tube 16 described above.

Each grasping member 120 may be attached at its proximal end to a respective actuation rod 122 extending within the outer tube 116 from a vertex 121 of the grasping member to a proximal end of the device (not shown). In the embodiment shown, each actuation rod 122 may have a threaded distal tip that is engaged into a tapped recess 123 (FIG. 5C) extending with a portion of the respective grasping member 120 adjacent the vertex 121 thereof, such that each actuation rod is removably coupled to the respective grasping member. The actuation rods 122 may be slidably coupled to one another by a coupling member such as the ring 24 described above.

Each grasping member 120 may have an V-shape when in the retracted position within the outer tube 116, as shown in FIG. 4, and each grasping member may assume a substantially linear shape when deployed from the outer tube, as shown in FIG. 5A. In that regard, each grasping member 120 may be formed from a memory metal or a strong, resilient metal or polymer that will cause the V-shape to form automatically when deployed. Depending on the length L of each grasping member 120 (FIG. 5A) relative to the diameter of the lumen of the outer tube 116, the grasping members may each have an acute-angled shape, a right-angled shape, or an obtuse-angled shape when in the retracted position within the outer tube.

Although each grasping member 120 is shown as having a V-shape orientation when in the retracted position within the outer tube 116, that need not be the case. The grasping members may have any other shape or configuration when retracted within the outer tube, including for example, a U-shape or a Y-shape. It is preferred that the grasping members have a retracted shape such as a V, U, or Y that is capable of enclosing a portion of leaflet tissue therein when opposed ends of the grasping members are brought towards one another.

Figures 5B, 5C:
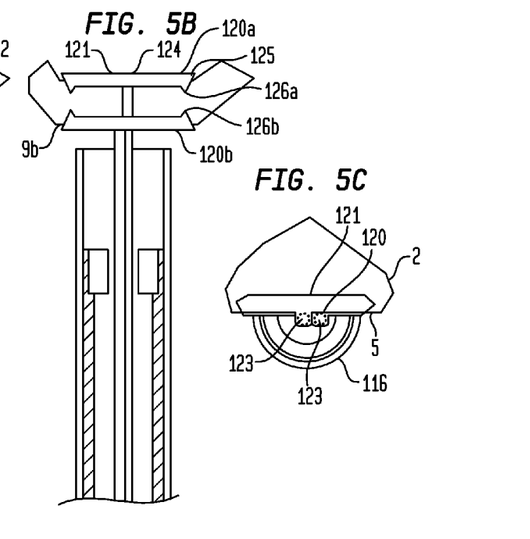
FIG. 5B is a longitudinal cross-sectional view of the device of FIG. 4, shown with both grasping members engaged with leaflet tissue.
FIG. 5C is a top view of FIG. 5B.

The opposed ends 125 of each grasping member 120 may be shaped into one or more barbs 126 that may extend from the central portion 124 of the grasping member in a direction substantially perpendicular to the plane of the central portion of the grasping member in the deployed position. For example, as shown in FIG. 5B, when the grasping members 120 are in the deployed position, the barbs 126a of a first grasping member 120a may extend proximally from the plane of the central portion 124, and the barbs 126b of a second grasping member 120b may extend distally from the plane of the central portion.

Although each grasping member 120 is shown as having one barb 126 at each of the opposed ends 125 thereof, that need not be the case. The invention contemplates grasping members each having only one barb, or each having more than two barbs, such as three, four, five, six, eight, ten, or twelve barbs. One or both of the grasping members may have several barbs adjacent to one another that together form a serrated surface. In an embodiment where each grasping member has only one barb, the barb of the first grasping member 120a may be at an opposite end 125 (on the left of FIG. 4, for example) than the barb of the second grasping member 120b (which may be on the right side of FIG. 4, for example).

The invention also contemplates grasping members having barbs not disposed at the ends 125 of the grasping members. Instead, one or more of the grasping members may have one or more barbs that are spaced apart from the ends of the grasping members. For example, one or more of the grasping members may have barbs at locations that are one-quarter and three-quarters of the distance along the grasping member between the opposed ends 125), and such grasping members may not have barbs disposed at the ends of the grasping members.

In the embodiment shown in FIG. 4, the releasable grasping members 120 may serve to help secure a captured portion of the posterior leaflet 2, in addition to serving as a capture tool. A tissue securing component in the form of a locking ring 130 may be configured to be applied around a captured portion of the posterior leaflet 2. The locking ring 130 may be removably disposed within the distal end of the lumen of a deployment tube 134. The locking ring 130 may be disposed on an annular shelf 136 adjacent the distal end of the deployment tube 134. The deployment tube 134 may be slidably disposed in the lumen of the outer tube 116 with a tight clearance.

To use the device 110 to gather heart valve leaflet tissue, the grasping members 120 may be threaded onto the distal ends of the respective actuation rods 122, and the locking ring 130 may be loaded into the lumen of the deployment tube 134 on the annular shelf 136.

Next, the distal portion 114 of the catheter assembly 112 may be inserted into a patient, for example, through the apex of the heart into the left ventricle, so that the distal portion extends between the posterior leaflet 2 and the anterior leaflet 3 of the mitral valve 1. The distal end 117 of the outer tube 116 may be disposed near the coaption line 5 of the mitral valve 1, similar to the position of the outer tube 16 shown in FIG. 3A, with the grasping members 120 oriented substantially parallel to the portion of the coaption line adjacent the distal end of the outer tube (e.g., such as the orientation of the grasping member shown in FIG. 5C).

Once the outer tube 116 has been properly positioned, the first grasping member 120a may be deployed by sliding the respective actuation rod 122 distally so that the grasping member slides beyond the distal end 117 of the outer tube 116. No longer being constrained by the outer tube 116, the first grasping member 120a may assume a substantially linear orientation, with the first grasping member located above the target portion of the posterior leaflet 2 to be captured, similar to the position of the grasping member 20 shown in FIG. 3B. Next, the barbs 126a of the first grasping member 120a may be engaged with the upper surface 9a of the target portion of the posterior leaflet 2, as shown in FIG. 5A, by moving the distal portion 114 of the catheter assembly 112 proximally relative to the posterior leaflet until the barbs contact the leaflet.

Then, the second grasping member 120b may be deployed by sliding the respective actuation rod 122 distally so that the grasping member slides beyond the distal end 117 of the outer tube 116. No longer being constrained by the outer tube 116, the second grasping member 120b may assume a substantially linear orientation, with the second grasping member located below the target portion of the posterior leaflet 2 to be captured. Next, the barbs 126b of the second grasping member 120b may be engaged with the lower surface 9b of the target portion of the posterior leaflet 2, as shown in FIG. 5B, by sliding the respective actuation rod 122 distally relative to the posterior leaflet until the barbs contact the leaflet.

The user may capture the target portion of the posterior leaflet 2 by sliding the actuation rod 122 of the first grasping member 120a proximally and sliding the actuation rod of the second grasping member 120b distally until the target leaflet portion is sandwiched between the grasping members.

Figure 5D:
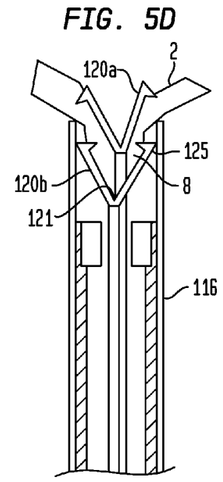
FIG. 5D is a longitudinal cross-sectional view of the device of FIG. 4, shown with both grasping members and the captured leaflet tissue retracted into the outer tube.

Subsequently, the grasping members 120 may be partially or entirely retracted into the lumen of the outer tube 116 along with the captured portion 8 of the posterior leaflet 2, as shown in FIG. 5D, so that the second grasping member 120b contacts the outer tube near the ends 125 of the second grasping member. As the grasping members 120 are retracted into the outer tube 116, contact between the second grasping member 120b and the outer tube 116 will cause the grasping members to bend at their respective vertexes 121 and assume a V-shape.

Figure 5E:
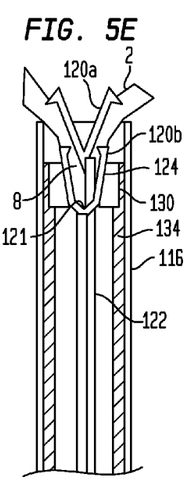
FIG. 5E is a longitudinal cross-sectional view of the device of FIG. 4, shown with the locking member deployed onto the grasping members and the captured leaflet tissue.

As shown in FIG. 5E, the user may secure the captured portion 8 of the posterior leaflet 2 by pushing the deployment tube 134 distally such that the vertex 121 of one or both of the grasping members 120 extends at least partially into the lumen of the deployment tube and into the center of the locking ring 130. The locking ring 130 may slide onto the V-shaped central portion 124 of the second grasping member 120b with a tight clearance, so that friction between the locking ring and the second grasping member will hold the locking ring in place and clamp the second grasping member tightly onto the captured portion 8 of the posterior leaflet 2. In a variant, the second grasping member 120b may include bumps or ribs extending along the central portion 124, so that when the locking ring 130 passes over the bumps or ribs, the bumps or ribs serve to retain the locking ring onto the second grasping member.

Figure 5F:
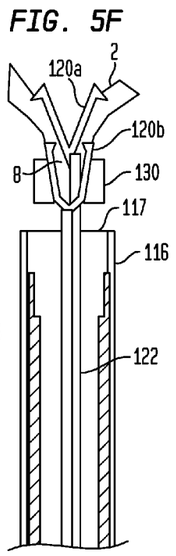
FIG. 5F is a longitudinal cross-sectional view of the device of FIG. 4, shown with the secured tissue released from the distal end of the outer tube.

After the locking ring 130 has been adequately secured on the second grasping member 120b, the device 10 may be withdrawn from the patient. As a first step, the grasping members 120, the locking ring 130, and the captured portion 8 of the posterior leaflet 2 may be removed from the lumen of the outer tube 116 by sliding the actuation rods 122 distally so that the grasping members slide beyond the distal end 117 of the outer tube 116, as shown in FIG. 5F.

Figure 5G:
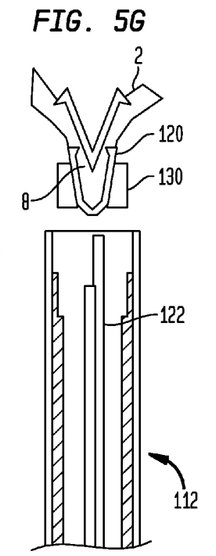
FIG. 5G is a longitudinal cross-sectional view of the device of FIG. 4, shown with the device disengaged from the secured tissue.

Next, the actuation rods 122 may be disengaged from the grasping members 120 by rotating the actuation rods about their longitudinal axes so that the distal ends of the actuation rods disengage from the recesses 123 of the grasping members, as shown in FIG. 5G. The catheter assembly 112 may subsequently be withdrawn from the patient through the apex of the heart. The procedure described above may be repeated to apply one or more additional sets of grasping members 120 and a locking ring 130 onto a different portion of the same posterior leaflet 2.

Although the locking ring 130 is described as having a fixed diameter and being configured to slide onto the V-shaped central portion 124 of the second grasping member 120b with a tight clearance, locking rings of other configurations may be used. For example, an expandable locking ring or clip may be used that is configured similarly as the clip 30 described above, such that it may be biased to curl into a substantially round configuration from a partially open configuration when deployed from the deployment tube 134. Such a clip may be initially disposed around an outer surface of the deployment tube 134 in a partially open configuration, and a second tube may be slidably disposed around the deployment tube with a tight clearance, such that the distal end of the second tube may be slid distally to push the clip off of the distal end of the deployment tube 134. Once the clip is pushed off of the deployment tube 134, such clip may clamp around the V-shaped central portion 124 of the second grasping member 120b with a tight clearance, so that friction between the clip and the second grasping member will hold the clip in place and clamp the second grasping member tightly onto the captured portion 8 of the posterior leaflet 2.

In the foregoing, particular structures have been described that are adapted to gather, secure, and repair heart valve leaflet tissue. The invention also contemplates the use of any alternative structures for such purposes, including structures having different lengths, shapes, and configurations.

Although the various gathering devices have been described herein in connection with tightening the posterior leaflet of a mitral valve, all of these devices may be used on other heart valve leaflets, such as the anterior leaflet of the mitral valve, or on any other tissue of the body for which a reduction in the length of the tissue would be beneficial.

Although the invention herein has been described with reference to particular embodiments in which the catheter assembly is inserted into the patient through the apex of the heart (i.e., transapical insertion), it is to be understood that the invention contemplates embodiments in which the catheter assembly extends through a portion of the vasculature of the patient to reach the heart, for example, through a transfemoral or subclavian artery, or a using transseptal procedure. Any other percutaneous technique for accessing the interior of the heart may also be used. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for gathering tissue of a heart valve leaflet, the device comprising:
   an outer tube extending in an elongated direction;
   a capture tool moveable in the outer tube between a contained position and a use position, the capture tool including two grasping members that are independently moveable relative to one another in the elongated direction and separable from the outer tube, each grasping member having a barb at each of two opposing ends thereof, the grasping members being operable to capture tissue of the heart valve leaflet therebetween with a first one of the grasping members located distally of the captured tissue with its barbs facing proximally and the second one of the grasping members located proximally of the captured tissue with its barbs facing distally and to draw the captured tissue into the outer tube in a gathered configuration so that the capture tool and the captured tissue collectively form a captured assembly;
   two actuation rods, each actuation rod being longitudinally slidable within the outer tube and adapted to be removably coupled to a respective one of the grasping members; and
   a tissue securing component disposed at a distal end of the outer tube and separable from the outer tube, the tissue securing component and the capture tool adapted to be separated from the outer tube together, the tissue securing component adapted to be applied to the captured assembly at least partially surrounding the capture tool to maintain the captured tissue in the gathered configuration, the tissue securing component being a locking ring that is configured to slide over at least one of the grasping members to lock the grasping members into the V-shape and to retain the captured tissue in the gathered configuration,
   wherein each grasping member is moveable between a retracted position in which the grasping member lies within the outer tube, and a deployed position in which the grasping member lies outside of the outer tube, each grasping member having a V-shape in the retracted position and extending substantially in a linear direction in the deployed position.

2. The device of claim 1, wherein a distal end of each actuation rod is threaded and adapted to engage with a tapped recess of the respective one of the grasping members.

3. A transcatheter method of gathering tissue of a heart valve leaflet, the method comprising:
   inserting an elongated catheter assembly to a position adjacent the heart valve leaflet, the catheter assembly including an outer tube extending in an elongated direction and a capture tool moveable in the outer tube between a contained position and a use position;
   moving the capture tool from the contained position to the use position, the capture tool including two grasping members that are independently moveable relative to one another in the elongated direction and separable from the outer tube, each grasping member having a barb at each of two opposing ends thereof, each grasping member being removably coupled to a respective actuation rod that is longitudinally slidable within the outer tube, each grasping member changing orientation or shape when moved from the contained position to the use position, the moving of the capture tool including first moving a first one of the grasping members from the contained position to the use position beyond a distal end of the outer tube, while a second one of the grasping members remains in the contained position within the outer tube, and then moving the second grasping member to the use position beyond the distal end of the outer tube;
   manipulating the catheter assembly so that tissue of the heart valve leaflet is captured by the capture tool, the first one of the grasping members located distally of the captured tissue with its barbs facing proximally, and the second one of the grasping members located proximally of the captured tissue with its barbs facing distally;
   retracting the capture tool from the use position toward the contained position to draw the captured tissue into the outer tube in a gathered configuration so that the capture tool and the captured tissue collectively form a captured assembly; and
   separating a tissue securing component from the distal end of the outer tube and applying the tissue securing component to the captured assembly at least partially surrounding the capture tool to maintain the captured tissue substantially in the gathered configuration, the tissue securing component and the capture tool adapted to be separated from the outer tube together, the tissue securing component being a locking ring,
   wherein the step of moving the capture tool from the contained position to the use position moves each grasping member from a V-shape to a substantially linear shape, and
   wherein the step of retracting the capture tool includes moving the grasping members into contact with the outer tube so that the grasping members move from the substantially linear shape to the V-shape, the locking ring being configured to slide over at least one of the grasping members to lock the grasping members into the V-shape and to retain the captured tissue in the gathered configuration.

4. The method of claim 3, wherein the step of applying the tissue securing component to the captured tissue includes sliding the locking ring over the at least one of the grasping members such that the grasping members are retained in the V-shape and the captured tissue is retained in the gathered configuration.

5. The method of claim 4, wherein the step of retracting the capture tool from the use position toward the contained position includes sliding the actuation rods in a proximal direction of the outer tube.

6. The method of claim 5, further comprising, after the step of applying the tissue securing component to the captured tissue, removing each actuation rod from a respective one of the grasping members.

* * * * *